(12) United States Patent
Cheng et al.

(10) Patent No.: US 7,531,519 B2
(45) Date of Patent: May 12, 2009

(54) POLYGALATENOSIDES AND USE THEREOF AS AN ANTIDEPRESSANT AGENT

(75) Inventors: Mo-Chi Cheng, Taipei (TW);
Feng-Nien Ko, Taipei (TW);
Tian-Shung Wu, Tainan (TW)

(73) Assignee: Medical and Pharmaceutical Industry Technology and Development Center, Taipei Hsien (TW)

( * ) Notice: Subject to any disclaimer, the term of this patent is extended or adjusted under 35 U.S.C. 154(b) by 477 days.

(21) Appl. No.: 11/524,470

(22) Filed: Sep. 21, 2006

(65) Prior Publication Data

US 2008/0076724 A1 Mar. 27, 2008

(51) Int. Cl.
*A61K 31/70* (2006.01)
*A01N 43/04* (2006.01)
(52) U.S. Cl. ............... 514/25; 536/4.1; 424/773
(58) Field of Classification Search ............ None
See application file for complete search history.

(56) References Cited

U.S. PATENT DOCUMENTS 7,175,861 B2 * 2/2007 Ko et al. ............. 424/773
7,179,496 B2 * 2/2007 Ko et al. ............. 424/773
7,223,425 B2 * 5/2007 Ko et al. ............. 424/773

\* cited by examiner

*Primary Examiner*—Patrick T Lewis

(74) *Attorney, Agent, or Firm*—Bacon & Thomas, PLLC

(57) ABSTRACT

A polygalatenoside useful as an antidepressant agent having the formula is disclosed:

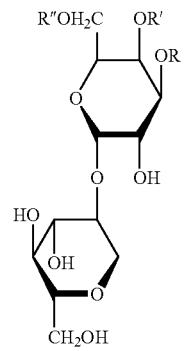

wherein R, R' and R" independently are H or $R_1$, provided that R, R' and R" are not all H, wherein $R_1$ is

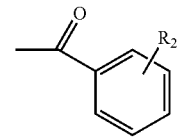

wherein $R_2$ is hydrogen, C1-C6 alkyl, C1-C6 alkoxy or halogen; or a pharmaceutically acceptable salt thereof. Preferably, $R_2$ is H.

21 Claims, 1 Drawing Sheet

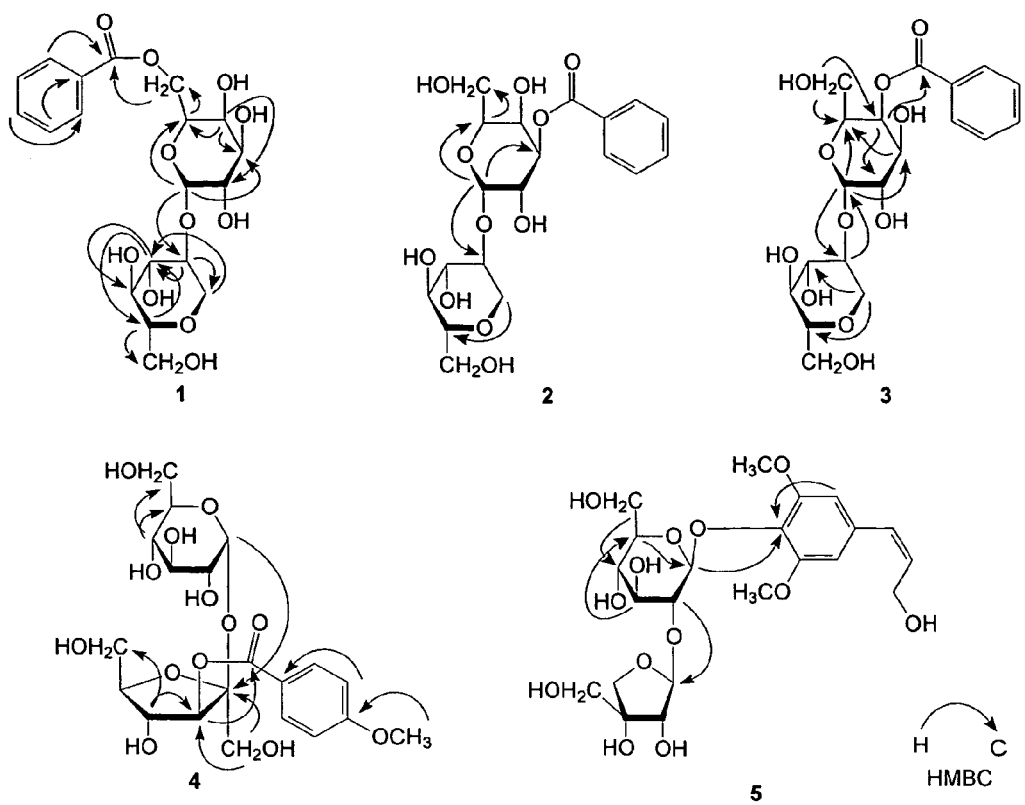
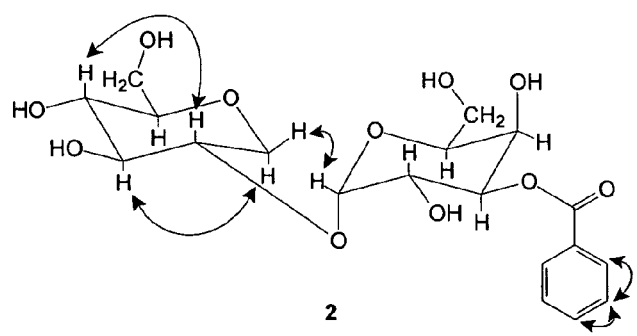
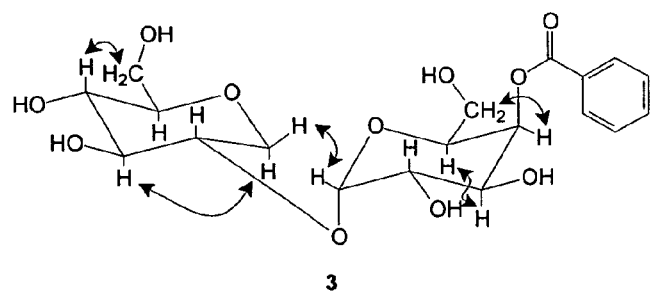
Figure 2

POLYGALATENOSIDES AND USE THEREOF AS AN ANTIDEPRESSANT AGENT

FIELD OF THE INVENTION

The present invention is related to novel polygalatenosides purified from a water-soluble extract from *Polygala*, and also to their anti-depression pharmaceutical use.

BACKGROUND OF THE INVENTION

Psychotic diseases such as anxiety and neurosis have increased in recent years, and various antidepressant medications are now available. A number of studies have demonstrated that the newer antidepressant agents, such as venlafaxine (norepinephrine reuptake inhibitor), and bupropion (norepinephrine/dopamine reuptake inhibitor), exert their actions through an interaction with multiple receptors within the central nervous system.

"Yuan Zhi" (the roots of *Polygala tenuifolia* Willd, Polygalaceae) is an important herb prescribed in the traditional Chinese medicine to mediate sedative, antipsychotic, cognitive improving, neuron protective, and anti-inflammatory therapeutic effects on the central nervous system. It has also been used for insomnia, neurasthenia, amnesia, palpitations with anxiety, restlessness, disorientation, and to prevent dementia and failure of memory. Various xanthones, saponins, and oligosaccharide esters have been reported from this plant. [Fujita, T.; Liu, D. Y.; Ueda, S.; Takeda, Y. *Phytochemistry* 1992, 31, 3997-4000; Ikeya, Y.; Sugama, K.; Okada, M.; Mitsuhashi, H. *Phytochemistry* 1991, 30, 2061-2065; Ikeya, Y.; Sugama, K.; Okada, M.; Mitsuhashi, H. *Chem. Pharm. Bull.* 1991, 39, 2600-2605; Miyase, T.; Iwata, Y.; Ueno, A. *Chem. Pharm. Bull.* 1991, 39, 3082-3084; Jiang, Y.; Tu, P. F. *Phytochemistry* 2002, 60, 813-816; Sakuma, S.; Shojji, J. *Chem. Pharm. Bull.* 1981, 30, 810-821; Jiang, Y.; Tu, P. *Chem. Pharm. Bull.* 2005, 53, 1164-1166; Jiang, Y.; Tu, P. *J. Asian Nat. Prod. Res.* 2003, 5, 279-283; Jiang, Y.; Zhang, W.; Tu, P. Xu, X. *J. Nat. Prod.* 2005, 68, 875-879.]

GB2383951A discloses an anti-depression pharmaceutical composition comprising a therapeutically effective amount of an active ingredient, in admixture with a pharmaceutically acceptable carrier or diluent for the active ingredient, in which the active ingredient is i) a polar solvent extract of *Polygala*, the polar solvent being water or a mixture of water and methanol or ethanol; ii) an aqueous fraction resulting from an extraction of the polar solvent extract with an organic solvent; iii) an organic eluate by introducing the polar solvent extract or the aqueous fraction into a reverse phase chromatography column, and eluting the column with water and an organic solvent; or iv) a filtrate having a molecular mass less than 30000 Dalton in the organic eluate.

U.S. Pat. No. 6,642,235 discloses methods and compositions for treating humans suffering from, or preventing a human from suffering, a physiological or psychiatric disease, disorder, or a condition where inhibiting reuptake of norepinephrine is a benefit. The physiological or psychiatric disease, disorder, or condition is selected from the group consisting of addictive disorders (including those due to alcohol, nicotine, and other psychoactive substances) and withdrawal syndrome, adjustment disorders (including depressed mood, anxiety, mixed anxiety and depressed mood, disturbance of conduct, and mixed disturbance of conduct and mood), age-associated learning and mental disorders (including Alzheimer's disease), anorexia nervosa, apathy, attention-deficit (or other cognitive) disorders due to general medical conditions, attention-deficit hyperactivity disorder (ADHD), bipolar disorder, bulimia nervosa, chronic fatigue syndrome, chronic or acute stress, chronic pain, conduct disorder, cyclothymic disorder, depression (including adolescent depression and minor depression), dysthymic disorder, fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder (GAD), incontinence (i.e., stress incontinence, genuine stress incontinence, and mixed incontinence), inhalation disorders, intoxication disorders (alcohol addiction), mania, migraine headaches, obesity (i.e., reducing the weight of obese or overweight patients), obsessive compulsive disorders and related spectrum disorders, oppositional defiant disorder, panic disorder, peripheral neuropathy, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), social phobia (including social anxiety disorder), specific developmental disorders, selective serotonin reuptake inhibition (SSRI) "poop out" syndrome (i.e., wherein a patient who fails to maintain a satisfactory response to SSRI therapy after an initial period of satisfactory response), and TIC disorders (e.g., Tourette's Disease).

SUMMARY OF THE INVENTION

A primary objective of the present invention is to provide novel polygalatenosides.

Another objective of the present invention is to provide an anti-depression pharmaceutical use of the novel polygalatenosides of the present invention.

In the present invention the inhibitory action of the methanol eluate of water soluble extract of roots of *P. tenuifolia* was investigated against $[^{125}I]$RTI-55 [3β-(4-iodophenyl)-tropan-2β-carboxylic acid methyl ester]-membrane protein binding. We report herein on the bioassay-guided separation of five new oligosaccharide derivatives (1-5) of extract from *P. tenuifolia* found to inhibit the $[^{125}I]$RTI-55 binding to norepinephrine transporter (abbreviated as NET hereinafter) protein. Among them compounds 1 and 2 were found more potent than the others.

BRIEF DESCRIPTION OF THE DRAWINGS

FIG. 1 shows Heteronuclear Multiple Bond Correlation (HMBC) correlations of the compounds 1-5 purified from a water soluble extract from the roots of *Polygala tenuifolia* according to the present invention.

FIG. 2 shows Nuclear Overhauser Effect Spectroscopy (NOESY) correlations of the compounds 1-5 purified from a water soluble extract from the roots of *Polygala tenuifolia* according to the present invention.

DETAILED DESCRIPTION OF THE INVENTION

The present invention provides a polygalatenoside having the following formula:

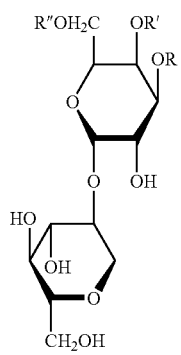

which comprises racemic mixture of optically active compounds or optically pure R and S stereoisomers, wherein R, R' and R" independently are H or $R_1$, provided that R, R' and R" are not all H, wherein $R_1$ is

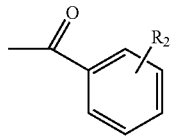

wherein $R_2$ is hydrogen, C1-C6 alkyl, C1-C6 alkoxy or halogen; or a pharmaceutically acceptable salt thereof.

Preferably, $R_2$ is hydrogen.
Preferably, R is $R_1$, and R' and R" are H.
Preferably, R' is $R_1$, and R and R" are H.
Preferably, R" is $R_1$, and R and R' are H.

The present invention further provides an antidepressant pharmaceutical composition comprising an anti-depression therapeutically effective amount of the polygalatenoside as defined by the above formula or a pharmaceutically acceptable salt thereof, as an active ingredient, in combination with a pharmaceutically acceptable carrier or diluent for the active ingredient.

The present invention further provides a method of treating a patient suffering depression comprising administering to the patient an antidepression therapeutically effective amount of the polygalatenoside as defined by the above formula or a pharmaceutically acceptable salt thereof.

The present invention further provides a method of treating a patient suffering a disease wherein inhibiting norepinephrine reuptake provides a benefit, the method comprising administering to the patient a therapeutically effective amount of the polygalatenoside as defined by the above formula or a pharmaceutically acceptable salt thereof as a norepinephrine reuptake inhibitor through blocking norepinephrine transport.

Preferably, said disease is addictive disorder, withdrawal syndrome, adjustment disorder, age-associated learning and mental disorder, anorexia nervosa, apathy, attention-deficit disorder, attention-deficit hyperactivity disorder (ADHD), bipolar disorder, or obesity.

[$^{125}$I]RTI-55-membrane binding assay-guided fractionation and separation of a water-soluble extract of the roots of *Polygala tenuifolia* gave five new oligosaccharide derivatives, polygalatenosides A-E (1-5). The structures of these new oligosaccharides were established on the basis of spectroscopic evidence. Polygalatenosides A and B (1 and 2) showed significant inhibitory activity with $IC_{50}$ values of 30.0 and 6.04 µM, respectively, in this membrane binding assay, and acted as norepinephrine reuptake inhibitors through blocking norepinephrine transport.

Experiments:

General Experimental Procedures. Optical rotations were recorded on a JASCO DIP-370 polarmeter. The UV spectra were recorded on a Hitachi UV-3210 spectrophotometer. The IR spectra were measured on a JASCO IR Report-100 spectrophotometer as KBr discs. HPLC was performed on a Shimadzu LC-10AT$_{VP}$ (Japan) system using a Cosmosil 5C-18-MS-II column (20×250 mm and 4.6×250 mm, 5 µm). $^1$H, $^{13}$C, HMQC, HMBC, and NOESY NMR spectra were recorded on Bruker AMX-400 and Varian-400 Unity Plus NMR spectrometers, using tetramethylsilane (TMS) as internal standard; all chemical shifts are reported in parts per million (ppm, δ). Mass spectra (EI or FAB) were performed on a VG 70-250 S spectrometer.

Plant Material. The roots of *P. tenuifolia* were purchased from a market in Taipei, Taiwan in May, 2003, and authenticated by Prof. C. S. Kuoh (Department of Life Science, National Cheng Kung University). A voucher specimen of the plant (No. 920021) has been deposited at the herbarium of Medical and Pharmaceutical Industry Technology and Development Center, Taipei County, Taiwan.

Extraction and Isolation. The air-dried roots of *P. tenuifolia* (1.25 kg) were powdered and extracted twice with $H_2O$ (5 L) for 2 h under reflux. The $H_2O$ extract was subjected to Diaion HP-20 column chromatography and eluted with $H_2O$ (45 L), 50% MeOH (30 L), and MeOH (25 L), successively. The 50% MeOH eluate was concentrated under reduced pressure to give a pale yellow syrup (44 g) and was chromatographed on a silica gel column (203-400 mesh, E. Merck, 800 g) using mixtures of $CHCl_3$/MeOH (80:20, 75:25, 70:30, 65:35, and 50:50) and 100% methanol to afford six fractions. Fraction 2 (1.0 g) was subjected to preparative HPLC [ODS-5 (20×250 mm)] using a mixture of $H_2O$/$CH_3CN$ as mobile phase ($H_2O$:$CH_3CN$=70:30, flow rate: 10 mL/min; UV 230 nm) to give three sub-fractions: 2-1 (125.3 mg), retention time of 5-13 minutes; 2-2 (121.3 mg), retention time of 13-18 minutes, and 2-3 (27.1 mg), retention time of 18-23 minutes. Sub-fraction 2-2 was separated by HPLC [column: ODS-5 (4.6×250 mm) with the mobile phase $H_2O$-MeOH (80:20); flow rate: 1.0 mL/min; UV: 230 nm] to afford 2 (retention time: 13.3 min) (3.1 mg), 5 (retention time: 17.7 min) (1.6 mg), 4 (retention time: 19.4 min) (3.8 mg), 3 (retention time: 20.9 min) (4.6 mg), and 1 (retention time: 22.2 min) (33.8 mg), successively, the structures of which are shown as follows:

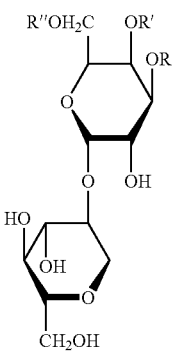

1 R = H, R' = H, R" = benzoyl
2 R = benzoyl, R' = H, R" = H
3 R = H, R' = benzoyl, R" = H

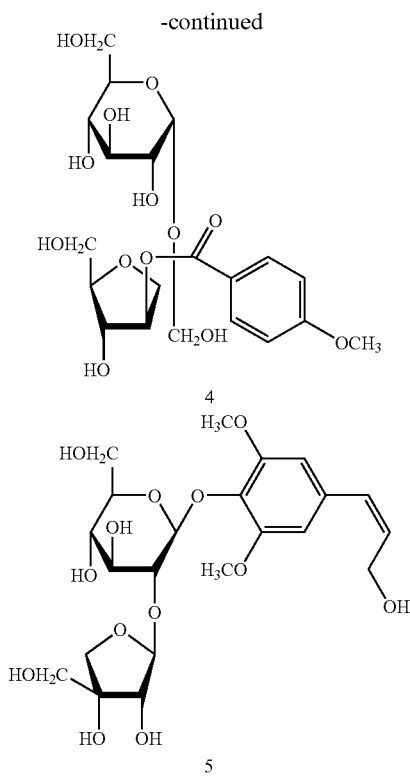

Polygalatenoside A (1): colorless syrup, $[\alpha]_D$+171 (c 0.01, MeOH); UV (MeOH) $\lambda_{max}$ (log ε) 228 (4.12), 273 (3.41), 279 (sh) (3.37) nm; IR (KBr) $v_{max}$ 3411, 1713, 1634, 1603, 1585, 1285, 1080 cm$^{-1}$; $^1$H and $^{13}$C NMR, see Tables 1 and 2; FABMS m/z 431 ([M+H]$^+$, 3), 307 (40), 291 (24), 289 (18), 267 (8), 154 (100), 139 (11), 138 (28), 137 (56), 136 (58), 107 (15); HRFABMS m/z 431.1557 [M+1]$^+$ (calcd for $C_{19}H_{27}O_{11}$, 431.1553).

Polygalatenoside B (2): colorless syrup, $[\alpha]_D$+343.1 (c 0.003, MeOH); UV (MeOH) $\lambda_{max}$ (log ε) 228 (3.94), 272 (3.69) nm; IR (KBr) $v_{max}$ 3415, 2927, 1713, 1602, 1452, 1280 cm$^{-1}$; $^1$H and $^{13}$C NMR, see Tables 1 and 2; FABMS m/z 431 [M+H]$^+$, 307, 291, 289, 154, 137, 136, 107; HRFABMS m/z 431.1552 [M+1]$^+$ (calcd for $C_{19}H_{27}O_{11}$, 431.1553).

Polygalatenoside C (3): colorless syrup, $[\alpha]_D$+256.6 (c 0.005, MeOH); UV (MeOH) $\lambda_{max}$ (log ε) 229 (3.87), 273 (3.72), 301 (3.55) nm; IR (KBr) $v_{max}$ 3402, 1713, 1631, 1602, 1452, 1280 cm$^{-1}$; $^1$H and $^{13}$C NMR, see Tables 1 and 2; FABMS m/z 431 ([M+H]$^+$, 3.4), 307 (33), 291 (21), 289 (15), 267 (8), 155 (27), 154 (100), 139 (11), 138 (29), 137 (57), 136 (61), 107 (16); HRFABMS m/z 431.1554 [M+1]$^+$ (calcd for $C_{19}H_{27}O_{11}$, 431.1553).

Polygalatenoside D (4): colorless syrup, $[\alpha]_D$+103.7 (c 0.004, MeOH); UV (MeOH) $\lambda_{max}$ (log ε) 216 (3.98), 258 (4.02) nm; IR (KBr) $v_{max}$ 3414, 1708, 1606, 1512, 1464 cm$^{-1}$; $^1$H and $^{13}$C NMR, see Tables 1 and 2; HRFABMS m/z 477.1606 [M+1]$^+$ (calcd for $C_{20}H_{29}O_{13}$, 477.1611).

Polygalatenoside E (5): colorless syrup, $[\alpha]_D$+616.8 (c 0.001, MeOH); UV (MeOH) $\lambda_{max}$ (log ε) 258 (4.15) nm; IR (KBr) $v_{max}$ 3400, 1585, 1505, 1464, 1405 cm$^{-1}$; $^1$H and $^{13}$C NMR, see Tables 1 and 2; FABMS m/z 505 ([M +H]$^+$, 0.5), 503 (2), 459 (3), 371 (3), 369 (3), 297 (4), 277 (11), 241 (16), 185 (100), 149 (28), 117 (10), 93 (98), 75 (40); HRFABMS m/z 505.1920 [M+1]$^+$ (calcd for $C_{22}H_{33}O_{13}$: 505.1923).

Membrane Binding Assay. Membranes from dog kidney MDCK cells, which stably transfected with the human norepinephrine transporter, were used. Total cell membranes were prepared from transfected cells grown to confluence in 500 cm$^2$ tissue culture dishes. Cells were scraped into centrifuge tube and pelleted at 900 g and 4° C. for 10 min. The pellets were resuspended in modified Tris-HCl buffer (50 mM Tris-HCl, 100 mM NaCl, 1 μM leupetin, 10 μM PMSF; pH 7.4), and centrifuged at 17000 g and 4° C. for 30 min. Then, the pellets were resuspended, homogenized with a glass homogenizer with a Teflon pestle and centrifuged at 17000 g and 4° C. for 90 minutes. Pellets were collected and resuspended in modified Tris-HCl buffer. Protein concentrations were determined using BCA protein assay reagent (Pierce, Rockford). For the binding assay, a 40 μg aliauot of membrane protein was incubated with 0.2 nM [$^{125}$I]RTI-55 [3β-(4-iodophenyl)-tropan-2β-carboxylic acid methyl ester] at 4° C. for 3 h. The binding was terminated by rapid vacuum filtration over Whatman GF/B filters soaked in 0.3% polyethylineimine followed by three rapid 1 mL washes in ice-cold buffer. Bound radioactivity was measured by gamma emission spectrometry. Non-specific binding was determined in the presence of 10 μM desipramine and was subtracted from the data in the absence of desipramine to yield specific binding.

Results:

The air-dried roots (1.25 kg) of *P. tenuifolia* were powdered and extracted with water under reflux. The water extract was subjected to Diaion HP-20 column chromatography and eluted, in turn, with H$_2$O, 50% aqueous MeOH, and 100% MeOH. The 50% aqueous MeOH eluate was chromatographed on a silica gel column using CHCl$_3$-MeOH to afford six fractions. Among them, the fraction 2 inhibited [$^{125}$I]RTI-55 binding to norepinephrine transporter in MDCK cells in a concentration-dependent manner. The IC$_{50}$ value was calculated to be 4.6 μg/mL. The selected fraction 2 was then subjected to preparative HPLC, using reversed-phase (ODS), which led to the isolation of five new oligosaccharide derivatives, polygalatenosides A-E (1-5).

Polygalatenoside A (1) was isolated as a colorless syrup. The HRFABMS of 1 showed a protonated molecular ion peak at m/z 431.1557 [M+H]$^+$, consistent with a molecular formula of $C_{19}H_{26}O_{11}$. The UV spectrum showed absorption maxima suggesting the presence of a benzoyl residue. In the IR spectrum, bands at 3411 and 1713 cm$^{-1}$ revealed the presence of hydroxyl and conjugated ester carbonyl groups. The $^1$H NMR spectrum displayed signals for a benzoyl group (γ 7.99, 2H d; 7.61, 1H, t; 7.47, 2H, d) in addition to signals due to galactosyl and polygolitosyl residues (Table 1). In addition, the $^{13}$C NMR signals due to benzoyl, galactosyl, and polygolitosyl moieties (Table 2) also indicated 1 to be a polygolitosylgalactoside of benzoic acid. All proton and carbon NMR signals were assigned by $^1$H—$^1$H COSY, HMQC, and HMBC NMR experiments. The downfield shift of C-2 of the polygolitosyl unit by 4 ppm compared to that of polygolitol,[18] and the downfield shift of C-1 of the galactosyl unit to δ$_C$ 95.7, suggested the interglycosidic linkage in 1 as polygolitosyl-(2→1)-α-galactoside. This was supported by a $^3$J correlation between H-1 of the galactosyl unit (δ$_H$ 5.00) and C-2 of the polygolitol moiety (δ$_C$ 73.3) in a HMBC experiment (FIG. 1). In the NMR spectra, downfield shifts of the methylene proton signals of the galactosyl residue to δ$_H$ 4.49 and 4.39 and its C-6 carbon to δ$_C$ 64.3, were used to establish the position of the benzoyl group linkage at C-6. This was confirmed by the $^3$J correlation between H-6 (δ$_H$ 4.49 and 4.39) and the ester carbonyl carbon of benzoyl residue (δ$_C$ 168.2).

Analysis of all the available data led us to conclude that polygalatenoside A (1) is 6-O-benzoyl polygolitosyl-(2→1)-α-galactose.

Polygalatenosides B (2) and C (3) were isolated as colorless syrups. The HRFABMS of 2 and 3 gave protonated molecular ion peaks at m/z 431.1552 and 431.1554 [M+H]$^+$, respectively, and their $^{13}$C NMR data were consistent with a molecular formula of $C_{19}H_{26}O_{11}$, the same as that of 1. The UV spectra each showed absorption maxima corresponding to a benzoyl residue. The IR bands at 3415 and 1713 cm$^{-1}$ indicated the presence of hydroxyl and conjugated ester carbonyl groups, respectively. In turn, the NMR spectra of polygalatenosides B and C were similar to those of 1 showing a benzoyl residue as an ester moiety, and galactosyl and polygolitosyl residues as sugar moieties. The substitution sites of these residues were decided with the aid of NOE (FIG. 2) and HMBC (FIG. 1) NMR observations after assignment of all proton signals from the $^1$H-$^1$H COSY and HMQC spectra. The appearance of downfield shifted signals for C-2 of the polygolitosyl and C-1 of the galactosyl moieties in the $^{13}$C NMR spectra and a $^3$J correlation between H-1 (galactosyl) and C-2 (polygolitosyl) in the HMBC spectra of both compounds 2 and 3 confirmed the sugar residues as polygolitosyl-(2→1)-α-galactoside, the same as in 1. However, these compounds were found to differ in the site of the ester linkages. In 2, the downfield shifts of the H-3 and C-3 signals of the galactosyl unit to δH 5.29 and δhd c 75.3, respectively, suggested that the benzoyl group is located at C-3 of the galactosyl residue. In 3, the signals of H-4 and C-4 of the galactosyl unit were shifted downfield to $\delta_H$ 5.59 and $\delta_C$ 73.5, respectively, and suggested that the benzoyl group is linked at the galactosyl C-4. This was supported by the $^3$J correlation between H-4 ($\delta_H$ 5.59) of the galactosyl unit and the carbonyl carbon of the benzoyl group C-7 ($\delta_C$ 167.9) in the HMBC spectrum. Accordingly, 2 was defined structurally as 3-O-benzoyl-polygolitosyl-(2→1)-α-galactose and 3 as 4-O-benzoyl-polygolitosyl-(2→1)-α-galactose.

Polygalatenoside D (4) was obtained as a colorless syrup. The HRFABMS displayed a protonated molecular ion at m/z 477.1606, corresponding to the molecular formula, $C_{20}H_{29}O_{13}$. The UV spectrum of 4 showed absorptions at 216 and 258 nm. The IR bands at 3414 and 1708 cm$^{-1}$ were consistent with the presence of hydroxyl and conjugated ester carbonyl groups. The $^1$H NMR spectrum displayed signals for $A_2B_2$-type aromatic protons (δ 8.06 and 7.01, each 2H), and a methoxy group (δ 3.86, 3H, s), in addition to signals due to a sucrose moiety. The $^{13}$C NMR spectrum of 4 also showed signals due to a p-methoxybenzoyl group and a sucrose residue (Table 2). Full assignments of the $^1$H and $^{13}$C NMR signals were secured by COSY, HMQC, and HMBC experiments. The presence of the downfield-shifted oxymethine proton and carbon (H-3 and C-3) of the fructosyl moiety at $\delta_H$ 5.56 and $\delta_C$ 80.6, respectively, suggested that the p-methoxybenzoyl moiety is located at C-3' in 4. This was supported by the HMBC spectrum, since H-3 of the fructosyl residue ($\delta_H$ 5.56) was correlated to an ester carbonyl carbon of a p-methoxybenzoyl moiety at $\delta_C$ 167.7. Thus, the structure of 4 was deduced as 3'-O-p-methoxybenzoyl-sucrose.

Polygalatenoside E (5) was isolated as colorless syrup, and was deduced as having an elemental composition of $C_{22}H_{32}O_{13}$ from its HRFABMS ([M+H]$^+$ m/z 505.1920). The IR absorption bands at 3400, 1585, 1505, and 1464 cm$^{-1}$ indicated the presence of hydroxyl and aromatic moieties. NMR data of 5 showed a cis-sinapyl alcohol moiety signals including two equivalent aromatic protons at $\delta_H$ 6.55 (2H, s), two methoxy groups at $\delta_H$ 3.83 (6H, s), two cis-olefinic protons at $\delta_H$ 6.48 (1H, d, J=11.6 Hz) and 5.80 (1H, dt, J=11.6, 6.4 Hz), and oxymethylene protons at $\delta_H$ 4.34 (2H, dd, J=6.4, 1.6 Hz), in addition to signals of a glucosyl at $\delta_C$ 103. 2, 79.2, 79.2, 71.8, 78.5, and 63.1, and an apiosyl at $\delta_C$ 110.9, 78.6, 81.4, 76.1, and 66.9 in $^{13}$C NMR spectrum of 5. By comparison of these data with those of kalopanaxin D [Kazuko, S.; Shuichi, S.; Yoshiteru I.; Junzo, S. *Chem. Pharm. Bull.* 1991, 39, 865-870], the sugar portion was deduced as a β-apiosyl-(1→2)-β-glucoside moiety. This was supported by the downfield shift of C-2 of glucosyl to $\delta_C$ 79.2 and $^3$J correlation between the H-2 proton ($\delta_H$ 3.69) of the glucosyl unit and the C-1 of the apiosyl ($\delta_C$ 110.9) unit in the HMBC experiment (FIG. 1). In addition, sinapyl alcohol was located at glucosyl C-1 based on the observed HMBC correlations between the glucosyl H-1 ($\delta_H$ 5.10) and the cis-sinapyl C-4 ($\delta_C$ 135.5). From these data, the structure of 5 was elucidated as sinapyl alcohol 4-O-β-apiosyl-(1→2)-β-glucose.

Compounds 1-5 were tested in vitro for their ability to inhibit isotope labeled RTI-55 binding to norepinephrine transporter protein [Galli, A.; Defelice L. J.; Duke, B. J.; Moore, K. R.; Blakely, R. D. *J. Exp. Biol.* 1995, 198, 2197-2212]. In this membrane-binding assay, polygalatenosides A (1) and B (2) showed significant inhibitory activities with $IC_{50}$ values of 30.0 and 6.04 μM, respectively. Desipramine, a tricyclic antidepressant, also inhibited [$^{125}$I]RTI-55 binding to NET with an $IC_{50}$ value of 0.93 nM. These results indicated that they may act as norepinephrine reuptake inhibitors by specific block blockage of NETs.

TABLE 1

$^1$H NMR Spectroscopic Data of 1-5 in CD$_3$OD

| Proton(s) | 1$^a$ | 2 | 3 | 4 | 5 |
|---|---|---|---|---|---|
| sugar moiety | | | | | |
| galactose-1 | 5.00 d (4.2) | 5.06 d (4) | 5.09 d (3.5) | — | — |
| 2 | 3.78 dd (10.8, 4.2) | 4.21 dd (10.5, 4) | 3.94 dd (9.5, 3.5) | — | — |
| 3 | 3.84 dd (10.8, 3.6) | 5.29 dd (10.5, 2.5) | 4.10 dd (9.5, 3.5) | — | — |
| 4 | 4.02 m | 4.25 br. | 5.59 br.s | — | — |
| 5 | 4.42 | 4.34 t (6) | 4.47 t (5.5) | — | — |
| 6 | 4.49 m | 3.78 dd (8.5, 6) | 3.57 d (5.5) | — | — |
|  | 4.39 m | 3.72 dd (8.5, 6) | 3.57 d (5.5) | — | — |
| polygolitol-1 | 4.03 m | 4.13 dd (11, 5) | 4.14 dd (11, 5) | — | — |
|  | 3.18 dd (11.4, 9.6) | 3.30 dd (11, 9) | 3.30 t (11) | | |
| 2 | 3.50 td (9.6, 5.4) | 3.68 td (9, 5) | 3.68 td (11, 6) | — | — |
| 3 | 3.43 (t (9.6) | 3.53 t (9) | 3.51 dd (11, 8.5) | | |
| 4 | 3.19 t (9.6) | 3.33 t (9) | 3.32 dd (8.5, 2) | | |
| 5 | 2.91 td (9.6, 1.8) | 3.22 dd (9, 6) | 3.23 dd (5.5, 2) | | |

TABLE 1-continued

¹H NMR Spectroscopic Data of 1-5 in CD₃OD

| Proton(s) | 1[a] | 2 | 3 | 4 | 5 |
|---|---|---|---|---|---|
| 6 | 3.45 dd (12.6, 9.6) | 3.86 d (12) | 3.86 d (12.5) | — | — |
|   | 3.72 dd (12.6, 1.8) | 3.64 dd (12, 6) | 3.60 dd (12.5, 5.5) | | |
| glucose-1 | — | — | — | 5.41 d (3.6) | 5.10 d (7.6) |
| 2 | — | — | — | 3.42 dd (9.2, 3.6) | 3.69 dd (9.2, 7.6) |
| 3 | — | — | — | 3.61 t (9.2) | 3.54 t (9.2) |
| 4 | — | — | — | 3.38 t (9.2) | 3.45 t (9.2) |
| 5 | — | — | — | 3.88 m | 3.16 ddd (9.2, 4.8, 2.4) |
| 6 | — | — | — | 3.76 dd (12, 4) | 3.62 dd (11.6, 4.8) |
|   | | | | 3.73 dd (12, 4.4) | 3.73 dd (11.6, 2.4) |
| fructose-1 | — | — | — | 3.67 d (12) | — |
|   | | | | 3.58 d (12) | |
| 2 | — | — | — | — | — |
| 3 | — | — | — | 5.56 d (7.6) | — |
| 4 | — | — | — | 4.42 t (7.6) | — |
| 5 | — | — | — | 3.96 ddd (7.6, 6, 3.2) | — |
| 6 | — | — | — | 3.83 brd (9.2) | — |
|   | | | | 3.81 dd (9.2, 6) | |
| apiose-1 | — | — | — | — | 5.47 br.s |
| 2 | — | — | — | — | 4.00 br. |
| 3 | — | — | — | — | — |
| 4 | — | — | — | — | 3.68 d (9.6) |
|   | | | | | 4.03 d (9.6) |
| 5 | — | — | — | — | 3.59 d (11.6) |
|   | | | | | 3.72 d (11.6) |
| aglycon moiety | | | | | |
| 2 | 7.99 d (8.4) | 8.12 d (7.5) | 8.06 d (7.5) | 8.06 dt (9.6, 2) | 6.55 s |
| 3 | 7.47 m | 7.50 t (7.5) | 7.50 t (7.5) | 7.01 dd (9.6, 2) | — |
| 4 | 7.61 m | 7.62 t (7.5) | 7.63 t (7.5) | — | — |
| 5 | 7.47 m | 7.50 t (7.5) | 7.50 t (7.5) | 7.01 dd (9.6, 2) | — |
| 6 | 7.99 d (8.4) | 8.12 d (7.5) | 8.06 d (7.5) | 8.06 dt (9.6, 2) | 6.55 s |
| 7 | — | — | — | — | 6.48 brd (11.6) |
| 8 | — | — | — | — | 5.80 dt (11.6, 6.4) |
| 9 | — | — | — | — | 4.34 dd (6.4, 1.6) |
| OMe | — | — | — | 3.86 s | 3.83 s |

[a]Recorded in D₂O.

TABLE 2

¹³C NMR Spectroscopic Data of 1-5 in CD₃OD

| carbon | 1[a] | 2 | 3 | 4 | 5 |
|---|---|---|---|---|---|
| sugar moiety | | | | | |
| galactose-1 | 95.7 | 97.8 | 98.9 | — | — |
| 2 | 67.9 | 67.6 | 70.5 | — | — |
| 3 | 69.1 | 75.3 | 69.7 | — | — |
| 4 | 69.2 | 68.8 | 73.5 | — | — |
| 5 | 68.7 | 72.0 | 71.4 | — | — |
| 6 | 64.3 | 62.4 | 62.1 | — | — |
| polygolitol-1 | 65.8 | 68.0 | 68.1 | — | — |
| 2 | 73.3 | 76.7 | 76.7 | — | — |
| 3 | 75.2 | 78.0 | 78.1 | — | — |
| 4 | 80.3 | 72.0 | 71.9 | — | — |
| 5 | 69.7 | 82.4 | 82.5 | — | — |
| 6 | 61.0 | 63.1 | 63.1 | — | — |
| glucose-1 | — | — | — | 93.9 | 103.2 |
| 2 | — | — | — | 73.6 | 79.2 |
| 3 | — | — | — | 75.4 | 79.2 |
| 4 | — | — | — | 71.6 | 71.8 |
| 5 | — | — | — | 75.2 | 78.5 |
| 6 | — | — | — | 62.7 | 63.1 |
| fructose-1 | — | — | — | 65.6 | — |
| 2 | — | — | — | 105.3 | — |
| 3 | — | — | — | 80.6 | — |
| 4 | — | — | — | 74.4 | — |
| 5 | — | — | — | 84.7 | — |
| 6 | — | — | — | 63.6 | — |
| apiose-1 | — | — | — | — | 110.9 |
| 2 | — | — | — | — | 78.6 |
| 3 | — | — | — | — | 81.4 |
| 4 | — | — | — | — | 76.1 |
| 5 | — | — | — | — | 66.9 |
| aglycon moiety | | | | | |
| 1 | 129.1 | 131.2 | 131.4 | 122.8 | 134.9 |
| 2 | 129.6 | 130.9 | 130.8 | 133.6 | 108.5 |
| 3 | 128.7 | 129.5 | 129.6 | 115.4 | 154.7 |
| 4 | 133.9 | 134.3 | 134.4 | 165.8 | 135.5 |
| 5 | 128.7 | 129.5 | 129.6 | 115.4 | 154.7 |
| 6 | 129.6 | 130.9 | 130.8 | 133.6 | 108.5 |
| 7 | 168.2 | 168.7 | 167.9 | 167.7 | 132.0 |
| 8 | — | — | — | — | 132.8 |
| 9 | — | — | — | — | 60.3 |
| OMe | — | — | — | 56.5 | 57.5 |

[a]Recorded in D₂O.

The invention claimed is:

1. A polygalatenoside having the following formula:

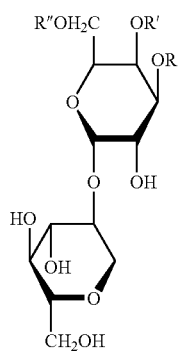

which comprises racemic mixture of optically active compounds or optically pure R and S stereoisomers,
wherein R, R' and R" independently are H or $R_1$, provided that R, R' and R" are not all H, wherein $R_1$ is

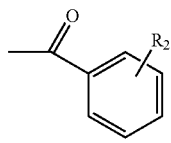

wherein $R_2$ is hydrogen, C1-C6 alkyl, C1-C6 alkoxy or halogen; or a pharmaceutically acceptable salt thereof.

2. The polygalatenoside or a pharmaceutically acceptable salt thereof, as claimed in claim 1, wherein $R_2$ is hydrogen.

3. The polygalatenoside or a pharmaceutically acceptable salt thereof, as claimed in claim 2, wherein R is $R_1$, and R' and R" are H.

4. The polygalatenoside or a pharmaceutically acceptable salt thereof, as claimed in claim 2, wherein R' is $R_1$, and R and R" are H.

5. The polygalatenoside or a pharmaceutically acceptable salt thereof, as claimed in claim 2, wherein R" is $R_1$, and R and R' are H.

6. An antidepressant pharmaceutical composition comprising an anti-depression therapeutically effective amount of a polygalatenoside or a pharmaceutically acceptable salt thereof as defined in claim 1, as an active ingredient, in combination with a pharmaceutically acceptable carrier or diluent for the active ingredient.

7. The composition as claimed in claim 6, wherein $R_2$ is hydrogen.

8. The composition as claimed in claim 7, wherein R is $R_1$, and R' and R" are H.

9. The composition as claimed in claim 7, wherein R' is $R_1$, and R and R" are H.

10. The composition as claimed in claim 7, wherein R" is $R_1$, and R and R' are H.

11. A method of treating a patient suffering depression comprising administering to the patient an antidepression therapeutically effective amount of a polygalatenoside or a pharmaceutically acceptable salt thereof as defined in claim 1.

12. The method as claimed in claim 11, wherein $R_2$ is hydrogen.

13. The method as claimed in claim 12, wherein R is $R_1$, and R' and R" are H.

14. The method as claimed in claim 12, wherein R' is $R_1$, and R and R" are H.

15. The method as claimed in claim 12, wherein R" is $R_1$, and R and R' are H.

16. A method of treating a patient suffering a disease wherein inhibiting norepinephrine reuptake provides a benefit, the method comprising administering to the patient a therapeutically effective amount of a polygalatenoside or a pharmaceutically acceptable salt thereof as defined in claim 1 as a norepinephrine reuptake inhibitor through blocking norepinephrine transport.

17. The method as claimed in claim 16, wherein $R_2$ is hydrogen.

18. The method as claimed in claim 17, wherein R is $R_1$, and R' and R" are H.

19. The method as claimed in claim 17, wherein R' is $R_1$, and R and R" are H.

20. The method as claimed in claim 17, wherein R" is $R_1$, and R and R' are H.

21. The method as claimed in claim 16, wherein said disease is addictive disorder, withdrawal syndrome, adjustment disorder, age-associated learning and mental disorder, anorexia nervosa, apathy, attention-deficit disorder, attention-deficit hyperactivity disorder (ADHD), bipolar disorder, or obesity.

* * * * *